US010242853B2

(12) United States Patent
Geromanos et al.

(10) Patent No.: US 10,242,853 B2
(45) Date of Patent: Mar. 26, 2019

(54) INTELLIGENT TARGET-BASED ACQUISITION

(71) Applicant: Waters Technologies Corporation, Milford, MA (US)

(72) Inventors: Scott J Geromanos, Middletown, NJ (US); Steven J Ciavarini, Natick, MA (US); Weibin Chen, Holliston, MA (US); Stephane Houel, Plymouth, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 15/318,254

(22) PCT Filed: Jun. 12, 2015

(86) PCT No.: PCT/US2015/035521
§ 371 (c)(1),
(2) Date: Dec. 12, 2016

(87) PCT Pub. No.: WO2015/191980
PCT Pub. Date: Dec. 17, 2015

(65) Prior Publication Data
US 2017/0125223 A1    May 4, 2017

Related U.S. Application Data

(60) Provisional application No. 62/011,681, filed on Jun. 13, 2014.

(51) Int. Cl.
*H01J 49/00*        (2006.01)
*G01N 30/86*        (2006.01)
*G01N 30/72*        (2006.01)

(52) U.S. Cl.
CPC ...... *H01J 49/0036* (2013.01); *G01N 30/8675* (2013.01); *G01N 30/8679* (2013.01);
(Continued)

(58) Field of Classification Search
CPC .................. H01J 49/0036; G01N 30/8675
(Continued)

(56) References Cited

U.S. PATENT DOCUMENTS

2010/0047812 A1* 2/2010 Van Eyk ............ G01N 33/6842
                                                        435/7.1
2011/0288779 A1* 11/2011 Satulovsky ......... H01J 49/0031
                                                        702/19
(Continued)

OTHER PUBLICATIONS

McQueen, et al ("Information-dependent LC-MS/MS acquisition with exclusion lists potentially generated on-the-fly: Case study using a whole cell digest of Clostridium thermocellum," Proteomics, 12, pp. 1160-1169, 2012).*
(Continued)

*Primary Examiner* — Michael Maskell

(57) ABSTRACT

A method of mass spectrometry comprises ionizing a sample eluting from a separation device in order to generate a plurality of parent ions. The method further comprises generating a target list of ions, which includes a predicted mass to charge ratio, a predicted chromatographic retention or elution time, and a predicted ion mobility drift time, derived from a model. Multiple cycles of operation are then performed as the sample elutes from the separation device. Each cycle of operation includes mass filtering the parent ions so that selected ions having mass to charge ratios within a first mass to charge ratio range are onwardly transmitted to a fragmentation or reaction device. The target list is then checked and the model is updated accordingly. The first mass to charge ratio range can then be adjusted in response to the updated model.

17 Claims, 14 Drawing Sheets

(52) U.S. Cl.
CPC ..... *G01N 30/8686* (2013.01); *G01N 30/8693* (2013.01); *H01J 49/0031* (2013.01); *G01N 30/72* (2013.01)

(58) Field of Classification Search
USPC .................................................. 250/281, 282
See application file for complete search history.

(56) References Cited

U.S. PATENT DOCUMENTS

| | | | |
|---|---|---|---|
| 2012/0259557 A1 | 10/2012 | Gorenstein et al. | |
| 2013/0299688 A1* | 11/2013 | Balogh ................. | H01J 49/168 250/282 |
| 2014/0034826 A1* | 2/2014 | Geromanos ........ | G01N 30/7233 250/282 |

OTHER PUBLICATIONS

Crowell, et al ("Increasing confidence of LC/MS identifications by using ion mobility spectrometry" Intl. J. Mass. Spectrom. vols. 354-355, Nov. 15, 2013, pp. 312-317).*
Extended European Search report for EP Application No. 15806361.0 dated Feb. 2, 2018.
McQueen, P., et al., "Information-dependent LC-MS/MS acquisition with exclusion lists potentially generated on-the-fly: Case study using a whole cell digest of Clostridium thermocellum", Proteomics, vol. 12, No. 8, pp. 1160-1169, Apr. 2012.
Crowell, K. L., et al., "Increasing confidence of LC-MS identifications by utilizing ion mobility spectrometry", International Journal of Mass Spectrometry, vol. 354-355, pp. 312-317, Jul. 5, 2013.

* cited by examiner

Simulator

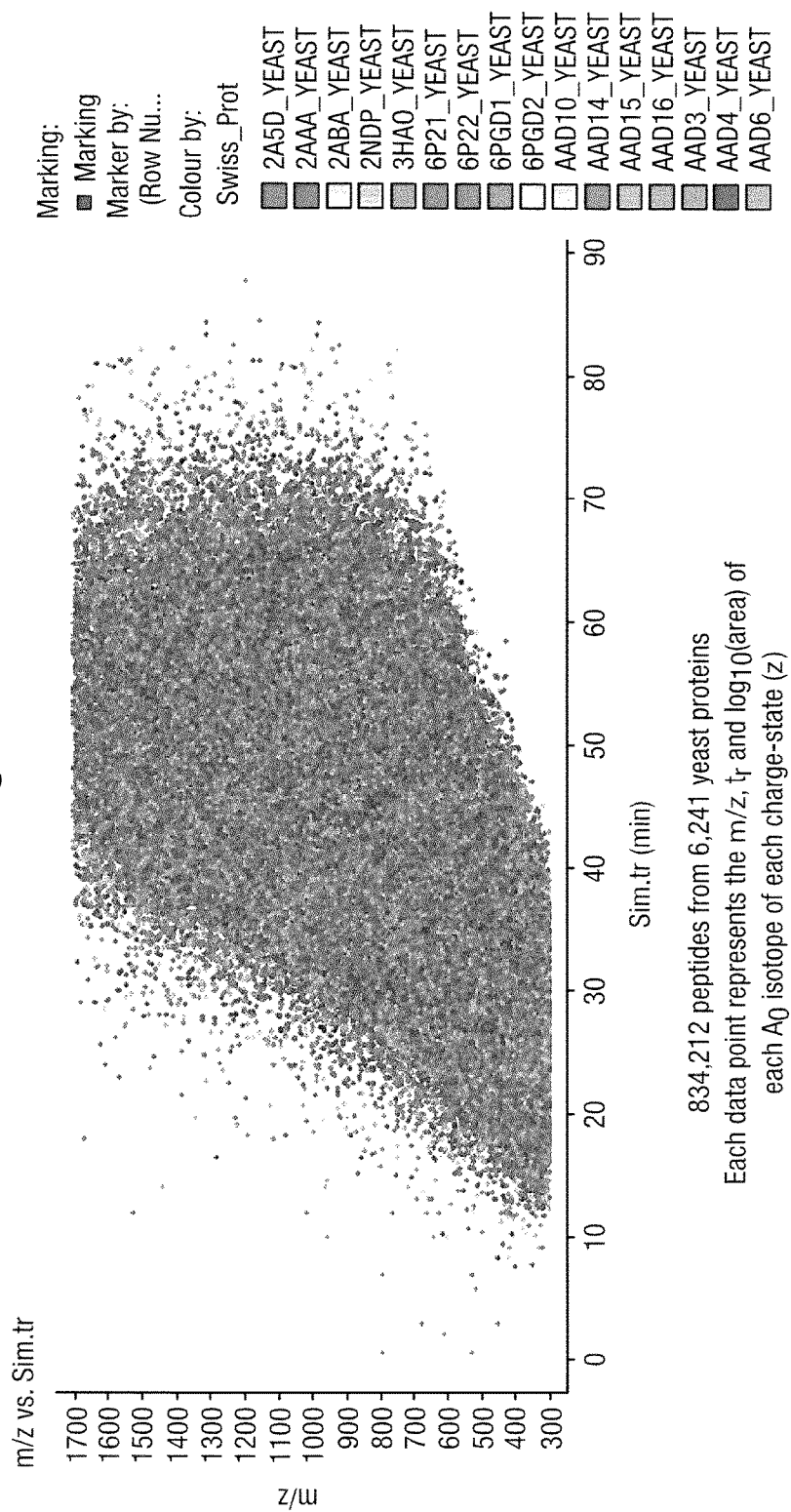

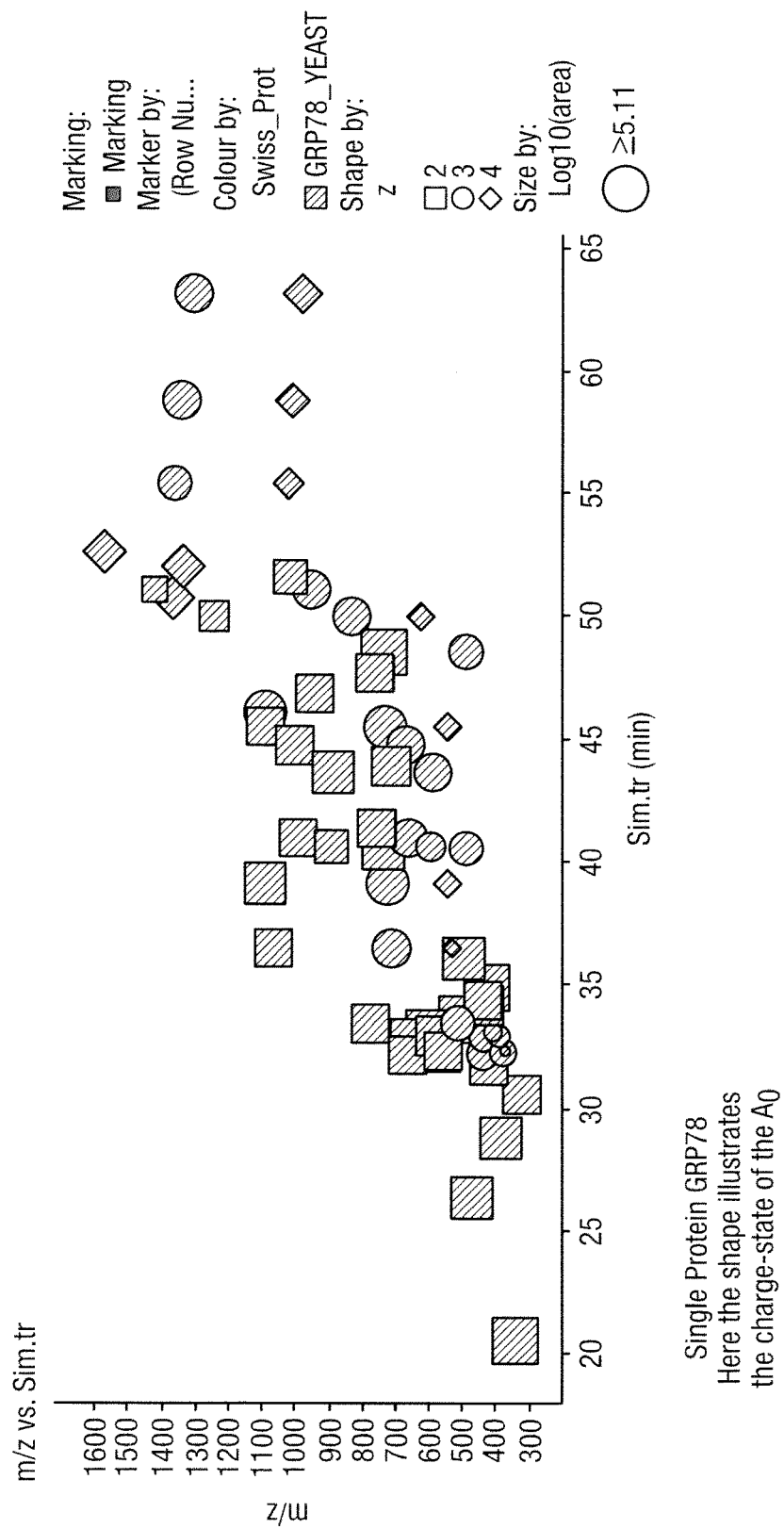

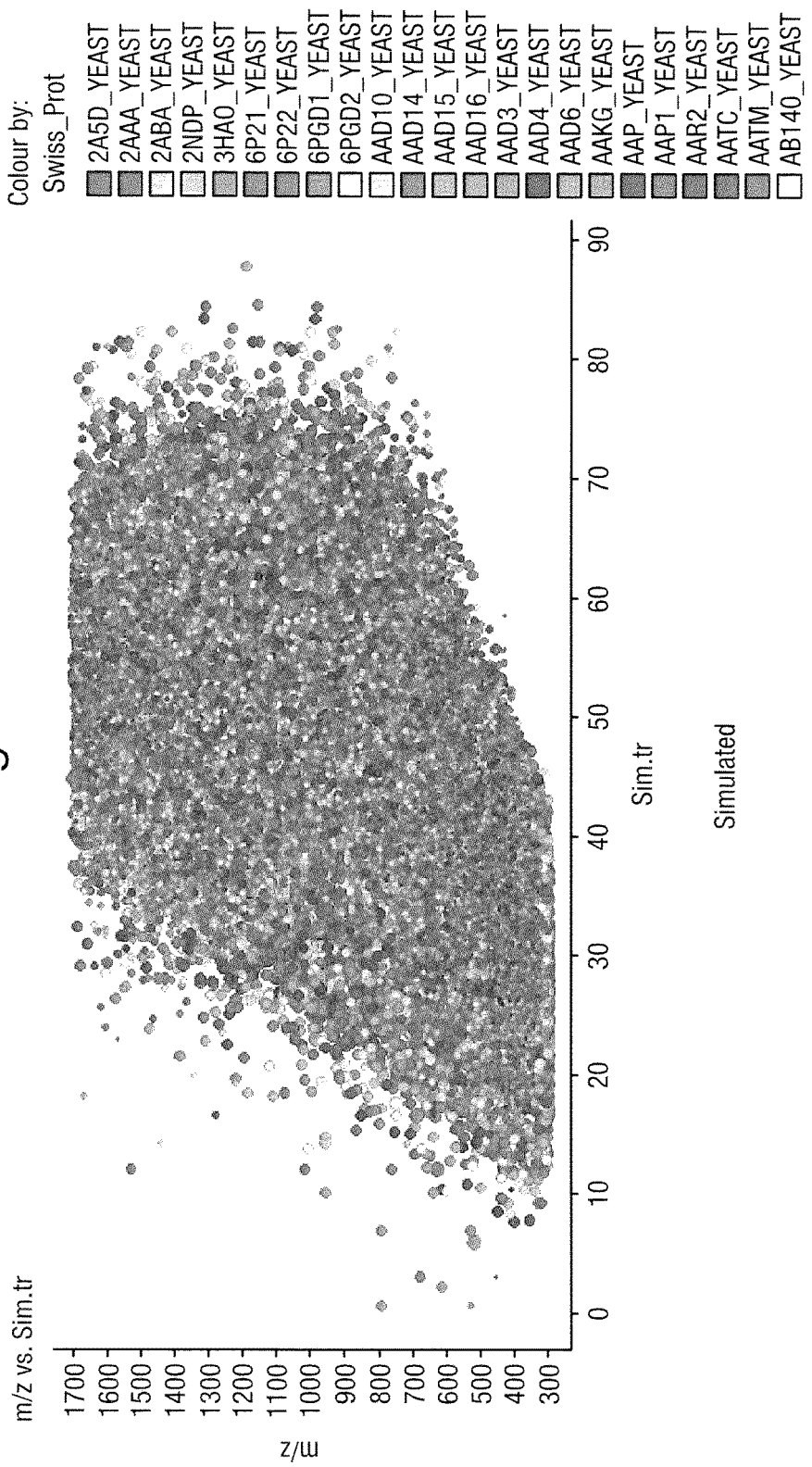

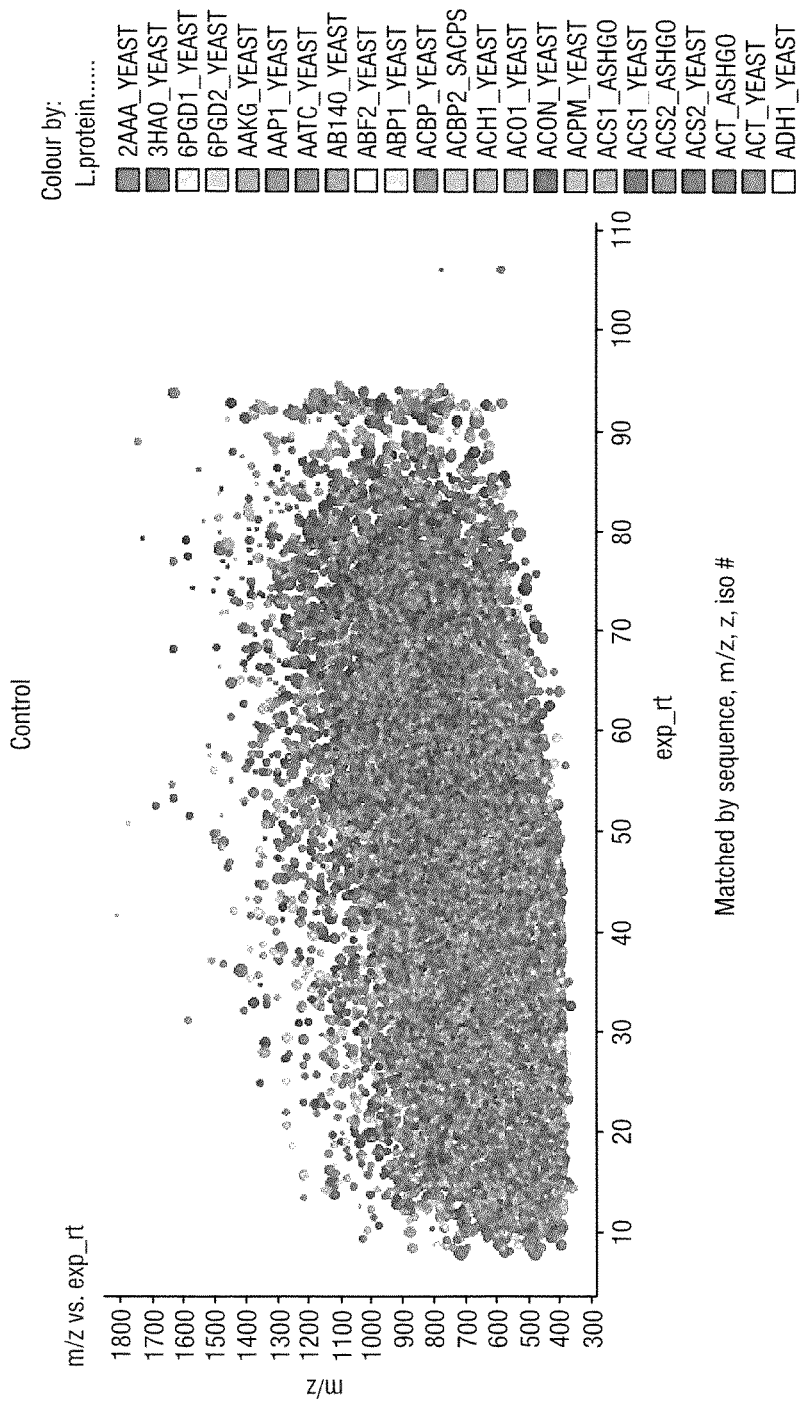

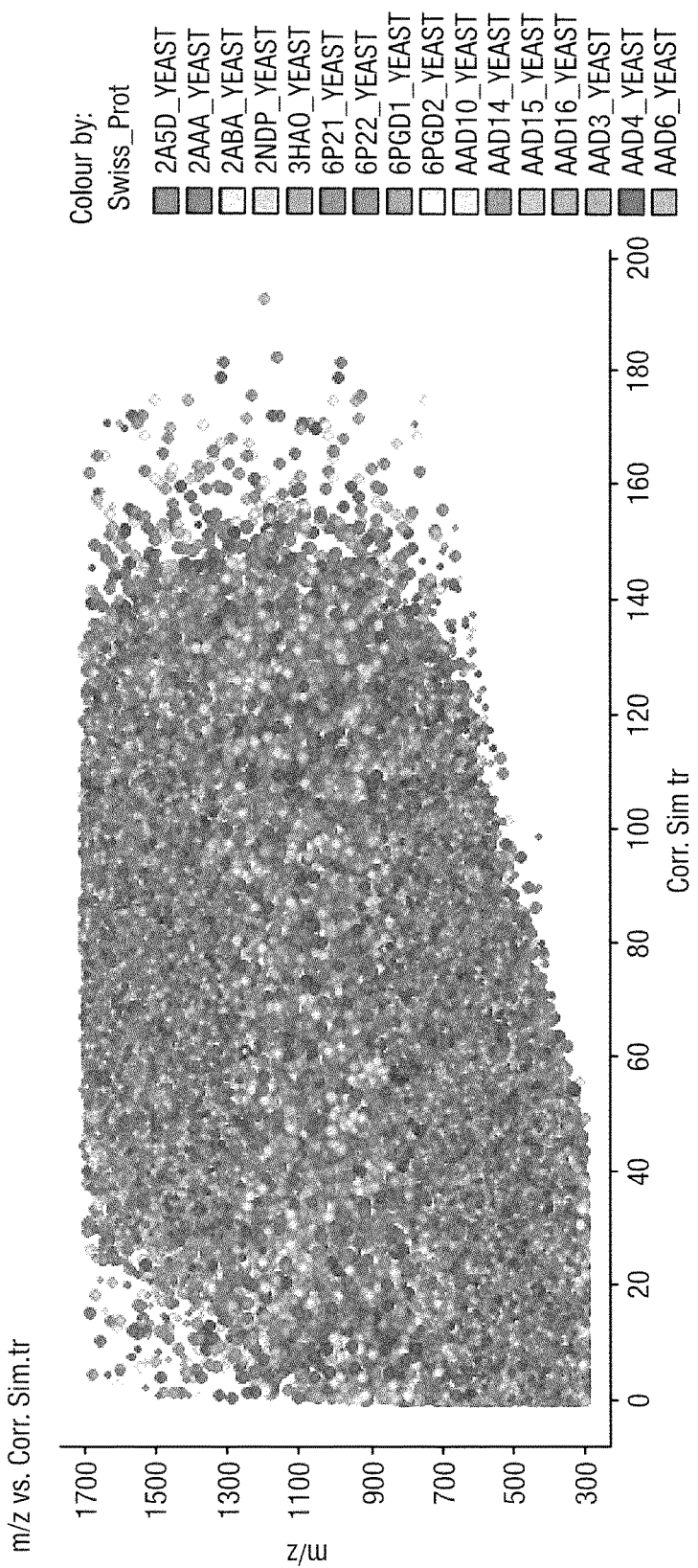

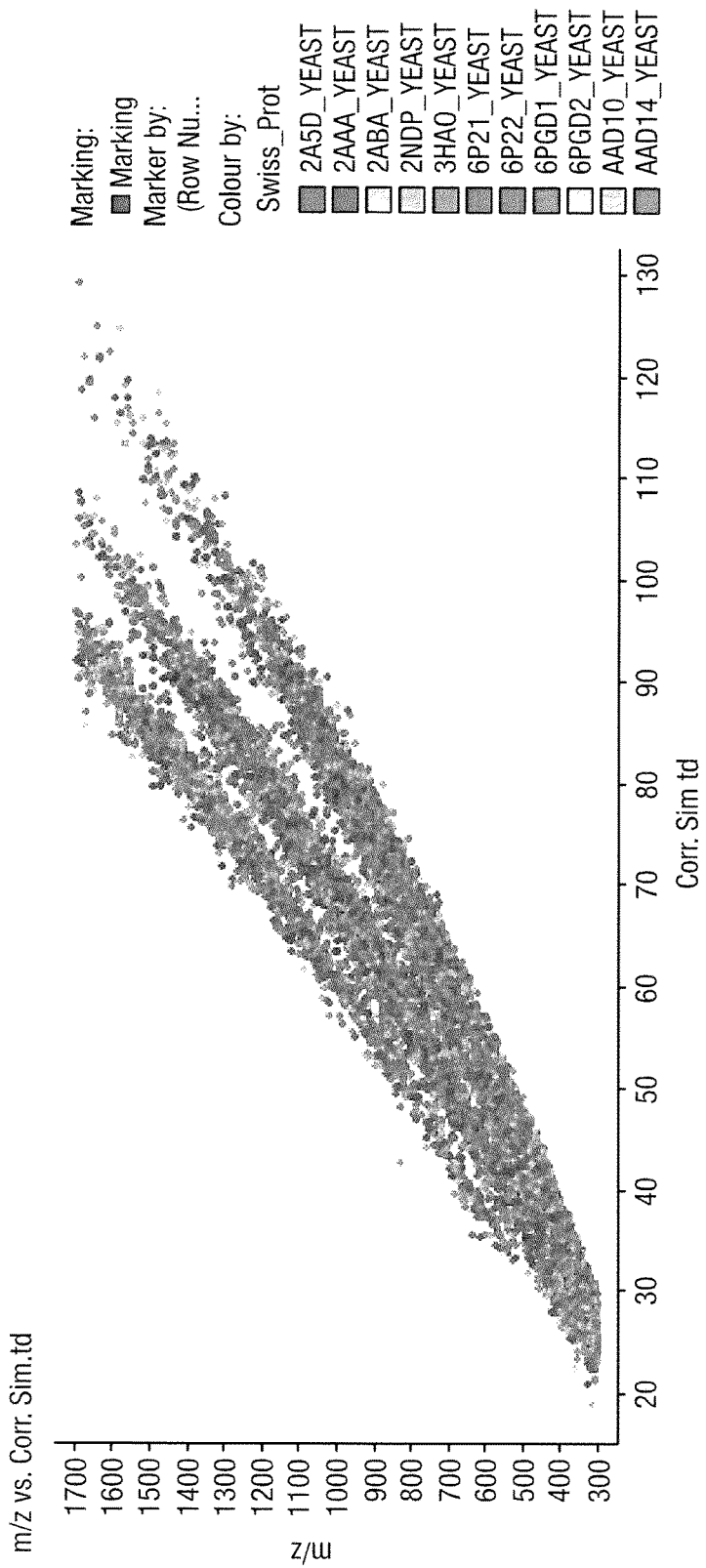

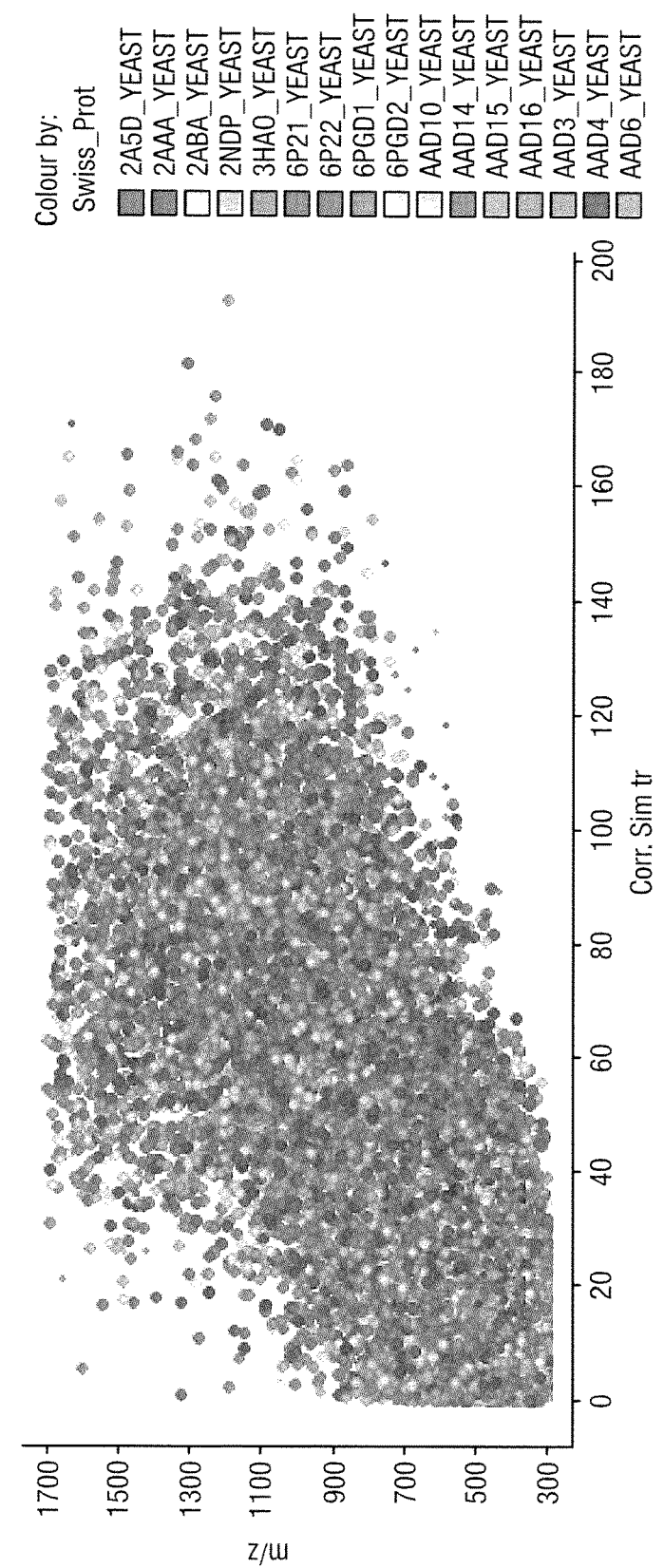

INTELLIGENT TARGET-BASED ACQUISITION

CROSS-REFERENCE TO RELATED APPLICATIONS

This application represents the U.S. National Phase of International Application number PCT/US2015/035521 entitled "Intelligent Target-Based Acquisition", filed 12 Jun. 2015, which claims priority from and the benefit of U.S. provisional patent application Ser. No. 62/011,681 filed on 13 Jun. 2014. The entire contents of these applications are incorporated herein by reference.

FIELD OF THE INVENTION

The present invention relates generally to a method of mass spectrometry and a mass spectrometer.

BACKGROUND

Conventional mass spectrometric analysis may be performed blindly such as top-n (n most intense, least intense) Data Dependent Acquisition ("DDA"), $MS^E$, $HDMS^E$ or SWATH Data Independent Acquisition ("DIA").

Alternatively, conventional mass spectrometric analysis may be performed in a targeted manner through Data Dependent Acquisition inclusion or exclusion lists which require prior knowledge of the elution time and mass to charge ratio of the targeted compounds.

It is desired to provide an improved method of mass spectrometry.

SUMMARY

According to an aspect there is provided a method of mass spectrometry comprising:

ionising a sample eluting from a separation device in order to generate a plurality of parent ions;

generating a target list of ions, wherein said target list comprises a predicted mass to charge ratio and at least one of: a predicted chromatographic retention or elution time; and a predicted ion mobility drift time, cross-sectional area or other data relating to ion mobility, derived from a model;

performing multiple cycles of operation as said sample elutes from said separation device, wherein each cycle of operation includes mass filtering said parent ions so that selected ions having mass to charge ratios within a first mass to charge ratio range are onwardly transmitted to a fragmentation or reaction device;

comparing or checking said target list and updating said model; and adjusting said first mass to charge ratio range and/or adjusting the width of said first mass to charge ratio range in response to said updated model.

In embodiments, the method may further comprise updating the target list so as to no longer select precursor or parent ions which are associated with previously identified parent compounds and/or may comprise updating the target list to select precursor or parent ions which are not associated with previously identified parent compounds.

In embodiments, the method may further comprise processing the target list and generating an initial time line, e.g. for the multiple cycles of operation. The method may further comprise sorting target ions by chromatographic retention or elution time and/or the intensity of the $A_0$ molecular ion of each charge group. The step of generating the initial time line may further comprise using peptide ionisation rank information. The step of generating the initial time line may further comprise prioritizing higher ionizing peptides from lower molecular weight proteins.

In embodiments, each cycle of operation may include mass filtering the parent ions based on the target list so that selected ions having mass to charge ratios within a first mass to charge ratio range are onwardly transmitted to a fragmentation or reaction device. Each cycle of operation may further include fragmenting or reacting the selected ions in or within the fragmentation or reaction device so as to form fragment or product ions. Each cycle of operation may further include obtaining parent ion and/or fragment or product ion mass spectral data. The step of comparing or checking the target list may involve comparing or checking the target list based on the ion mass spectral data. The step of comparing or checking the target list may further include identifying parent compounds using ion mass spectral data.

In embodiments, the target list may further comprise a predicted fragmentation pattern derived from a model. The model may include at least one of: a mass to charge ratio model; a chromatographic retention or elution time model; an ion mobility drift time model; and a fragmentation model.

In embodiments, each cycle of operation may further include separating and/or selecting parent ions and/or fragment or product ions according to their ion mobility. The method may further comprise adjusting a first ion mobility drift time range used to select parent ions and/or fragment or product ions and/or adjusting the width of a first ion mobility drift time range used to select parent ions and/or fragment or product ions in response to the updated model.

In embodiments, the model may be updated based on at least one of: a derived relationship between (i) modelled chromatographic retention or elution times and (ii) operational or experimental chromatographic retention or elution times; and a derived relationship between (i) modelled ion mobility drift times and (ii) operational or experimental ion mobility drift times. The derived relationship may be derived using a line of best fit (e.g. least squares).

According to an embodiment there is provided a system and method for the simultaneous acquisition of both global and highly-selective targeted mass spectrometry analysis of the entire component complement of both simple and complex mixtures.

The method may utilize enhanced modelling of the physicochemical attributes of biomolecules in conjunction with the increased peak capacity afforded by highly orthogonal workflows encompassing very high pressure liquid chromatography separations, high ion transfer, ion mobility and increased mass resolution using either a hybrid $DDA/MS^E$ or a $HD-DDA/HD-MS^E$ acquisition strategy.

According to an example workflow target compounds for proteomics analysis are input as a .fasta file of the proteome or proteins of interest as well as the enzyme used for enzymatic degradation.

According to an example workflow target compounds for small molecules such as metabolites and lipids are input as a .csv, .xlsx, .opa or .xml file optionally including a description and elemental composition.

Additional information may be included such as the gradient length, gradient slope, buffer composition, column type, mass resolving power and ion mobility separation ON/OFF. The additional information may be presented as input into a "Simulator" which comprises a series of modelling algorithms producing a target component list containing each compound predicted elution time, mass to charge ratio values (isotopes and charge groups) and cross-sectional area if ion mobility separation is employed.

The targeted list drives which ions are selected as well as the width of the isolation window during the Data Dependent Acquisition phase of a hybrid acquisition. Included in the embedded acquisition computer are the complete precursor and product ion envelopes for each predicted compound.

Upon completion of the Data Dependent Acquisition phase of a hybrid acquisition, the acquired ion list may be compared against that of the targets and if validated the chromatographic retention time and ion mobility drift time models are recalculated and the ion selection windows in mass to charge ratio, chromatographic retention time and ion mobility drift time may be adjusted accordingly.

The on-the-fly tuning of the attribute modelling algorithms allows for ever increasing precision in predicting the location of the targeted compounds in the impending three dimensional space of mass to charge ratio, chromatographic retention time and ion mobility drift time.

It will be understood that mass to charge ratio, cross-sectional area (and with respect to reverse phase chromatography hydrophobicity) are all physico-chemical constants.

The three-dimensional space between any pair of known compounds should be predictable and as such may be utilised to both validate identity and re-order, re-structure or amend the look-up table for future precursor ion selection.

According to an embodiment the target list may be continually updated to select upcoming precursor ions not associated with previously identified parent compounds. In the example of a proteomics experiment of, for example, a total cellular extract or a bio-fluid there are many known proteins whose peptides can be used as molecular beacons for the on-the-fly tuning of the modelling algorithm.

Given that the proteins in these experiments have been digested with an enzyme of known selectivity, then the algorithm may know with increasing precision where each previously identified protein's companion peptides will elute in chromatographic retention time and/or ion mobility drift time and chromatographic retention time. This continuing knowledge allows the algorithm to recurrently update the lookup table to ensure the greatest depth of coverage with respect to validating the presence of the proteins on the targeted include list while still spending enough time in the global HD-MS$^E$ (ion mobility) mode of acquisition for accurate area-under-the-curve quantification. Once the targeted proteins have been identified, the global HD-MS$^E$ data along with the highly accurate prediction models for ion mobility drift time and chromatographic retention time may be exploited to maximize sequence coverage as well as to query for known chemical or post-translational modifications or possible sequence variants.

According to another aspect there is provided a mass spectrometer comprising:

an ion source arranged and adapted to ionise a sample eluting from a separation device in order to generate a plurality of parent ions; and a control system arranged and adapted:

(i) to generate a target list of ions, wherein said target list comprises a predicted mass to charge ratio and at least one of: a predicted chromatographic retention or elution time; and a predicted ion mobility drift time, cross-sectional area or other data relating to ion mobility, derived from a model;

(ii) to perform multiple cycles of operation as said sample elutes from said separation device, wherein each cycle of operation includes mass filtering said parent ions so that selected ions having mass to charge ratios within a first mass to charge ratio range are onwardly transmitted to a fragmentation or reaction device;

(iii) to compare or check said target list and update said model; and (iv) to adjust said first mass to charge ratio range and/or to adjust the width of said first mass to charge ratio range in response to said updated model.

According to another aspect there is provided a method of mass spectrometry comprising:

ionising a sample eluting from a separation device in order to generate a plurality of parent ions;

generating a target list of ions, wherein the target list comprises a predicted chromatographic retention time or elution time, a predicted mass to charge ratio and optionally a predicted ion mobility drift time, cross-sectional area or other data relating to ion mobility;

performing multiple cycles of operation as the sample elutes from the separation device, wherein each cycle of operation includes mass filtering the parent ions so that ions having mass to charge ratios within a first mass to charge ratio range are onwardly transmitted to a fragmentation or reaction device;

comparing or checking the target list and updating a chromatographic retention time model and optionally updating an ion mobility drift time model; and adjusting the first mass to charge ratio range and/or adjusting the width of the first mass to charge ratio range in response to the updated chromatographic retention time model and optionally the updated ion mobility drift time model.

According to another aspect there is provided a mass spectrometer comprising:

an ion source arranged and adapted to ionise a sample eluting from a separation device in order to generate a plurality of parent ions; and a control system arranged and adapted:

(i) to generate a target list of ions, wherein the target list comprises a predicted chromatographic retention time or elution time, a predicted mass to charge ratio and optionally a predicted ion mobility drift time, cross-sectional area or other data relating to ion mobility;

(ii) to perform multiple cycles of operation as the sample elutes from the separation device, wherein each cycle of operation includes mass filtering the parent ions so that ions having mass to charge ratios within a first mass to charge ratio range are onwardly transmitted to a fragmentation or reaction device;

(iii) to compare or check the target list and update a chromatographic retention time model and optionally update an ion mobility drift time model; and (iv) to adjust the first mass to charge ratio range and/or to adjust the width of the first mass to charge ratio range in response to the updated chromatographic retention time model and optionally the updated ion mobility drift time model.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a VVien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage may have an amplitude selected from the group consisting of: (i) <about 50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0

MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

According to an embodiment analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to an embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments will now be described, by way of example only, and with reference to the accompanying drawings in which:

FIG. 1B shows 834,212 peptides from 6241 yeast proteins wherein each data point represents the mass to charge ratio, chromatographic retention time $t_r$ and $\log_{10}$(area) of each $A_0$ molecular ion or isotope of each charge state z and FIG. 1C shows the mass to charge ratio versus chromatographic retention time $t_r$ relating to a single protein GRP78, wherein ions having a $2^+$, $3^+$ and $4^+$ charge state are indicated;

FIG. 2A shows the mass to charge ratio versus simulated chromatographic retention time, FIG. 2B shows the mass to charge ratio versus experimental chromatographic retention time.

FIG. 3B shows a plot of mass to charge ratio versus corrected simulated chromatographic retention time, FIG. 3C shows a plot of mass to charge ratio versus corrected simulated ion mobility drift time and FIG. 3D shows a plot of mass to charge ratio versus corrected simulated chromatographic retention time wherein the plots are limited to the five best ionizing $A_0$;

DETAILED DESCRIPTION

An embodiment will now be described.

Figure 1A:
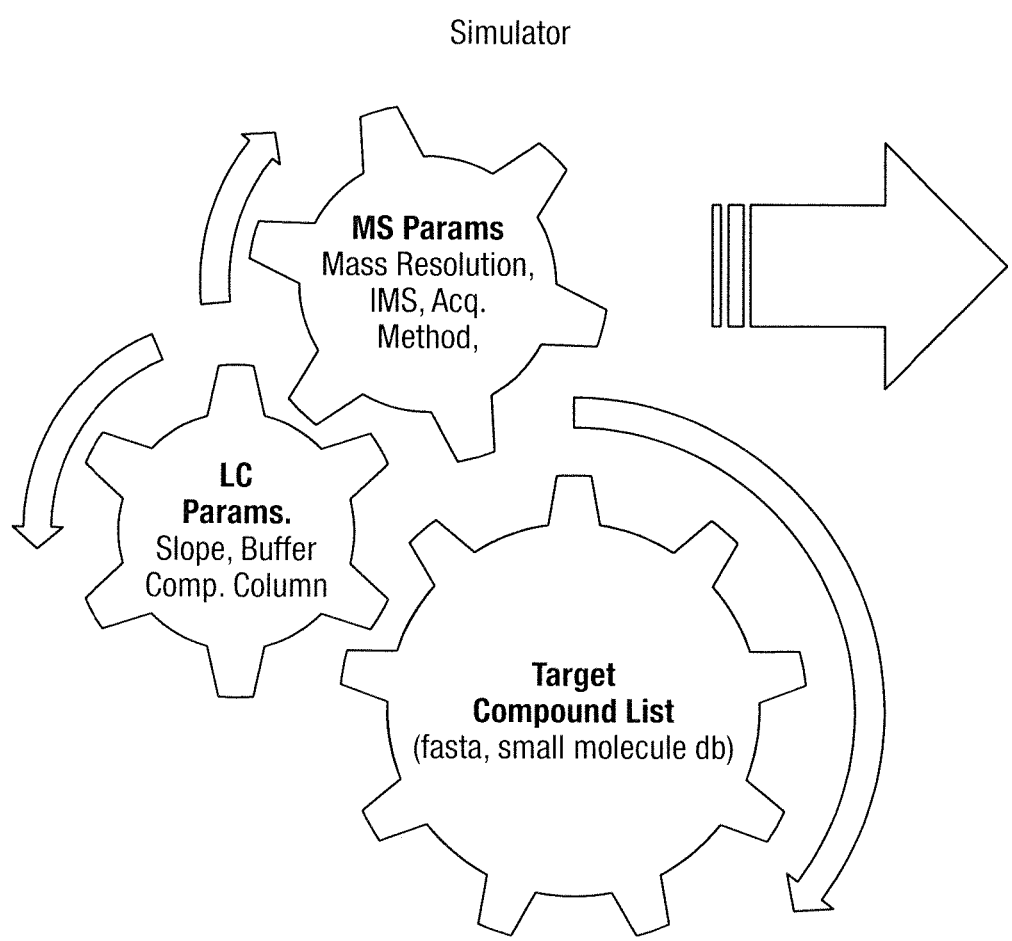
FIG. 1A shows elements of a model or "Simulator" comprising mass spectrometry parameters, liquid chromatography parameters and a target compound list.

According to an example workflow target compounds for proteomics analysis are input as a .fasta file of the proteome or proteins of interest as well as the enzyme used for enzymatic degradation in a manner as shown in FIG. 1A.

Target compounds for small molecules such as metabolites and lipids may be input as a .csv, .xlsx, .opa or .xml file optionally including a description and elemental composition.

Additional information may be included such as the gradient length, gradient slope, buffer composition, column type, mass resolving power, and whether ion mobility separation is ON/OFF. The data may be input into the "Simulator" which may comprise a series of modelling algorithms which produces a target component list containing each compound predicted chromatographic elution time $t_r$, mass to charge ratio values (isotopes and charge groups) and optionally also cross-sectional area if ion mobility separation ("IMS") is employed.

The targeted list drives which ions are selected as well as the width of the isolation window during a Data Dependent Acquisition portion of a hybrid acquisition. Included in the embedded acquisition computer are the complete precursor and product ion envelopes for each predicted compound.

Upon completion of a Data Dependent Acquisition portion of a hybrid acquisition, the acquired ion list may be compared against that of the targets and if validated the chromatographic retention time and ion mobility drift time models are recalculated and the ion selection windows in mass to charge ratio, retention and drift time may be adjusted accordingly.

The on-the-fly tuning of the attribute modelling algorithms allows for ever increasing precision in predicting the location of the targeted compounds in the impending three dimensional space of mass to charge ratio, chromatographic retention time $t_r$ and ion mobility drift time $t_d$.

It will be understood that mass to charge ratio and cross-sectional area (and with respect to reverse phase chromatography hydrophobicity) are physico-chemical constants.

The three-dimensional space between any pair of known compounds should be predictable and as such may be utilised to both validate identity and re-order, re-structure or amend a look-up table for future precursor ion selection.

According to an embodiment the target list may be continually updated to select upcoming precursor ions not associated with previously identified parent compounds. In the example of a proteomics experiment of, for example, a total cellular extract or a bio-fluid there will be many known proteins whose peptides can be used as molecular beacons for the on-the-fly tuning of the modelling algorithm.

Given that the proteins in these experiments have been digested with an enzyme of known selectivity, then the algorithm according to an embodiment may know with increasing precision where each previously identified protein's companion peptides will elute in chromatographic retention time and/or ion mobility drift time and chromatographic retention time. This continuing knowledge allows the algorithm to recurrently update the lookup table to ensure the greatest depth of coverage with respect to validating the presence of the proteins on the targeted include list while still spending enough time in a global HD-MS$^E$ (ion mobility) mode of acquisition for accurate area-under-the-curve quantification. Once the targeted proteins have been identified, the global HD-MS$^E$ data along with the highly accurate prediction models for ion mobility drift time and chromatographic retention time may be exploited to maximize sequence coverage as well as to query for known chemical or post-translational modifications or possible sequence variants.

For small molecule applications like lipids or metabolites the input may be a formatted *.xml, *.csv or *.opa file which optionally includes a name, description, elemental composition and if known, charge-state(s) and fragmentation pattern(s).

For a proteomics experiments the input may comprise a *.fasta file containing the target protein(s) sequence(s).

Various retention-time prediction models for different types of biological compounds are known.

A prediction model for chromatographic retention time and ion mobility drift time, isotope and charge distributions, fragmentation pathways, product ion coverage, ionization efficiency and n-linked glycosylation's for similar classes of biological compounds has been developed.

The targeting file as well as a number of user defined inputs (e.g. gradient slope and length, on-column load, IMS on/off and mass resolving power etc.) may be inputted into the "Simulator" and a target list may be generated.

The targeted list may then be processed by the "Scheduler". The "Scheduler" may generate an initial time line for intelligent time-based acquisition. Target ions may be sorted by retention-time (ascending) and intensity of the $A_0$ isotope (descending) of each charge group (ionization and charge distribution models).

The "Scheduler" may attempt to maximize the number of proteins that can be identified per unit time by restricting which peptides of a protein can be targeted in a given time interval. The peptide ionization model in the "Simulator" annotates each peptide to a protein with its ionization index number (best-to-least). Given that the best chance of identifying a protein in a complex sample is to select for targeted analysis it's best ionizing peptide, the "Scheduler" uses each peptides' ionization rank to assist in the creation of the initial time line. The "Scheduler" also takes into consideration the number of peptides generated from each protein and may prioritize the higher ionizing peptides from lower molecular weight proteins given that the number of opportunities for targeted selection is limited. Placement on the initial time line does not guarantee targeted selection only the opportunity for selection as such the time line or targeted list has to be dynamic.

This can be accomplished utilizing a number of different embodiments. According to an embodiment this may be accomplished on-the-fly where the product ion spectra of the target compounds resides in the acquisition computer internal to the mass analyzer.

According to an embodiment this may be accomplished by acquisition intervals where the product ion spectra of the target compounds resides on a second processing computer.

With respect to acquisition intervals the processing algorithm may start after a user or algorithmically defined time interval has passed. According to an embodiment in an automated fashion the processing software may wait until $\frac{1}{20}^{th}$ of the gradient elution time has passed. The data may then be extracted and processed. Validated target peptides are then used for updating the chromatographic retention time, ion mobility drift time and fragmentation models. Regardless of the variation in change of each predicted attribute (initial model to $n^{th}$ iteration) the models may be continually updated with each time block.

The constant re-modeling according to an embodiment corrects for any variations in temperature, pump performance, mixing or any other gradient creations problems that may arise during the analysis.

The targeted list resides both in the acquisition computer internal to the mass analyzer and external in the processing computer. Once updated the internal targeted ion list may be updated and transmitted back to the acquisition computer. Given the lack of elemental variability in biomolecules there will exist instances where a targeted ion is not what was predicted regardless of the accuracy of the models' prediction. Understanding that time is critical in maximizing the selectivity of targeting, and in some experiments ion mobility separation is not employed in precursor ion selection prior to Data Dependent Acquisition, in an example hybrid workflow ion mobility separation is employed in the MS1 channel (survey Data Dependent Acquisition, low-energy DIA) as such the processing algorithm first looks at the drift time associated to the selected precursor if the drift time is within the match window the product ion spectra are compared for validation else the processing algorithm moves on to the next targeted precursor. In instances where there is no ion mobility separation employed the processing algorithm compares all product ion spectra for every targeted precursor against its predicted compound.

FIG. 1A shows details of the "Simulator" including the input of mass spectrometry parameters, liquid chromatography parameters and a target compound list.

FIG. 1B shows the mass to charge ratio versus chromatographic retention time $t_r$ relating to 834,212 peptides from 6241 yeast proteins.

FIG. 1C shows the mass to charge ratio versus chromatographic retention time $t_r$ relating to a single protein GRP78. Ions having a $2^+$, $3^+$ and $4^+$ charge state are indicated.

FIG. 2A shows the mass to charge ratio versus simulated chromatographic retention time and FIG. 2B shows the mass to charge ratio versus experimental chromatographic retention time.

Figure 2C:
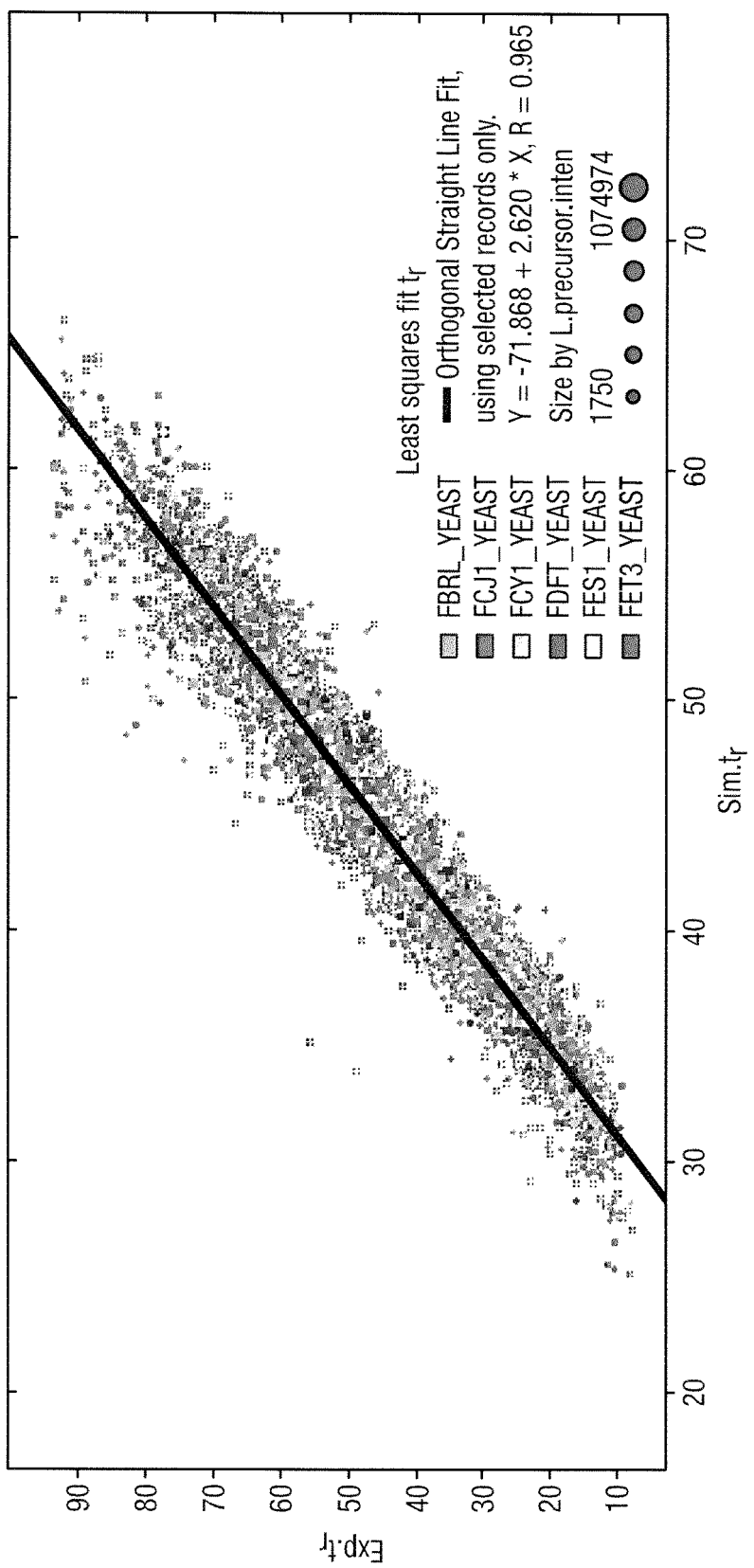
FIG. 2C shows a least squares fit of experimental chromatographic retention time versus simulated chromatographic retention time and FIG. 2D shows a least squares fit of experimental ion mobility drift time versus simulated ion mobility drift time.

FIG. 2C shows a least squares fit of experimental chromatographic retention time versus simulated chromatographic retention time.

Figure 2D:
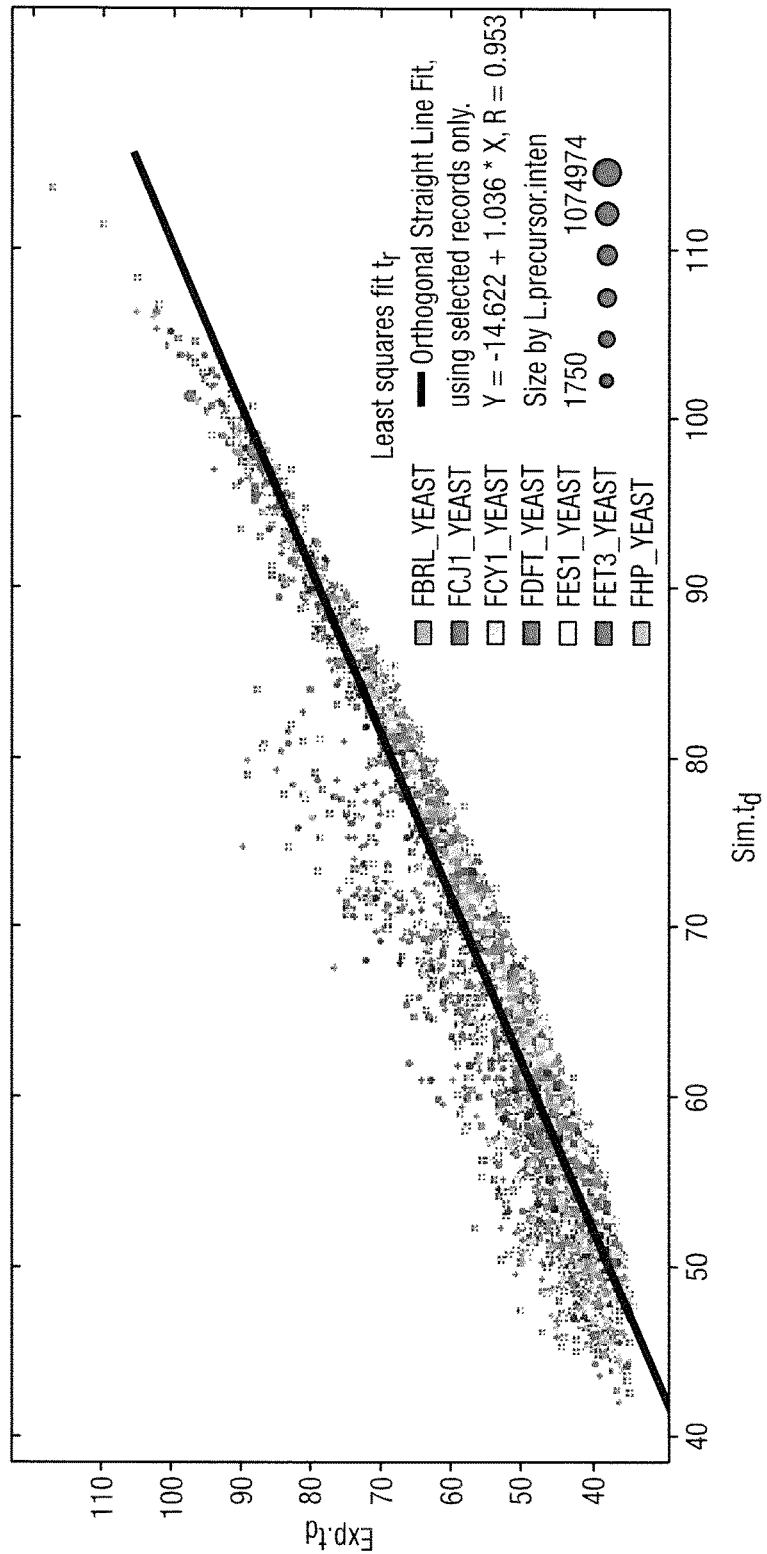

FIG. 2D shows a least squares fit of experimental ion mobility drift time versus simulated ion mobility drift time.

Figure 3A:
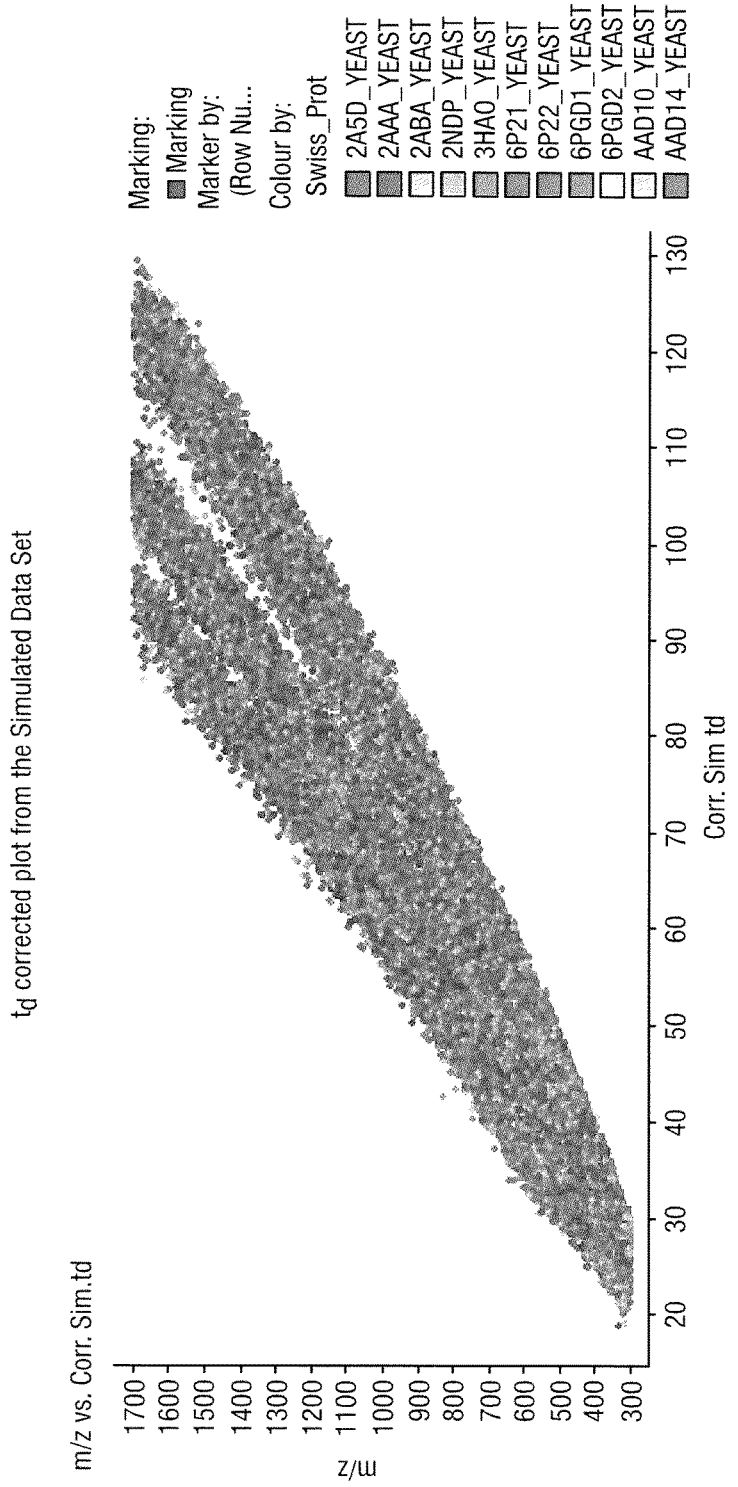
FIG. 3A shows a plot of mass to charge ratio versus corrected simulated ion mobility drift time.

FIG. 3A shows a plot of mass to charge ratio versus corrected simulated ion mobility drift time. FIG. 3B shows a plot of mass to charge ratio versus corrected simulated chromatographic retention time.

It is noted that the corrected simulated data as shown in FIG. 3B exhibits a better correlation between mass to charge ratio and chromatographic retention time than the initial simulated data shown in FIG. 2A. In particular, the data shown in FIG. 3B now passes through the origin and the range of chromatographic retention times has been lengthened.

FIG. 3C shows a plot of mass to charge ratio versus corrected simulated ion mobility drift time and FIG. 3D shows a plot of mass to charge ratio versus corrected simulated chromatographic retention time wherein the plots are limited to the five best ionizing $A_0$.

It is apparent from comparing FIG. 3C to FIG. 3A and from comparing FIG. 3D to FIG. 3B that limiting to the five best ionizing $A_0$ ions results in a further significant improvement in predicting or modeling the relationship between expected chromatographic retention time and expected ion mobility drift time and mass to charge ratio.

Figure 4:
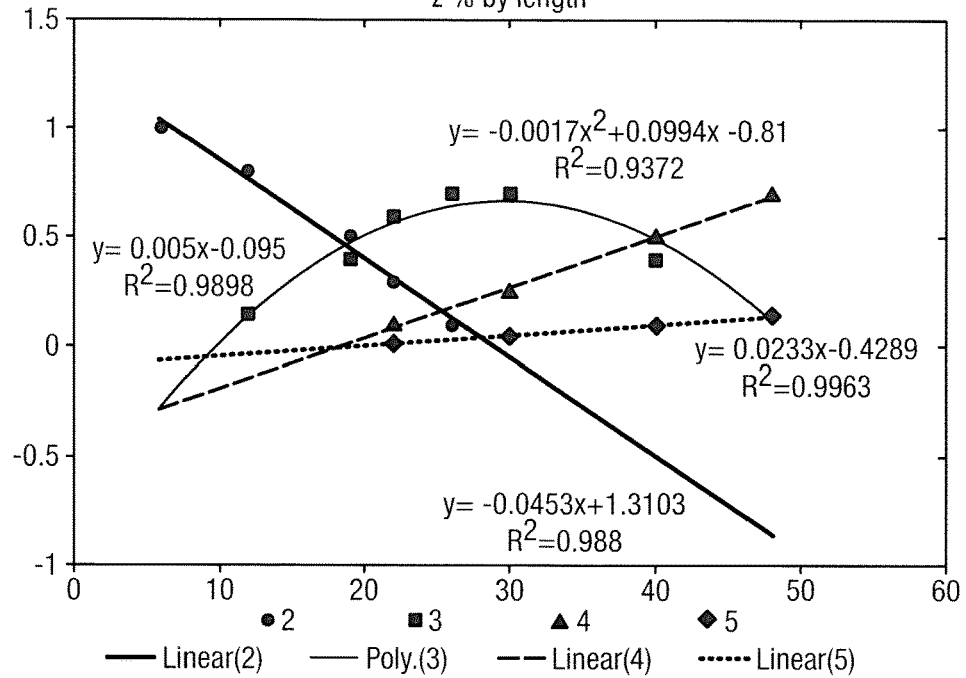
FIG. 4 shows z-distribution and ionisation model updates from matched sequences of mass to charge ratio, chromatographic retention time $t_r$, ion mobility drift time $t_d$ and charge state z.
Figure 4:
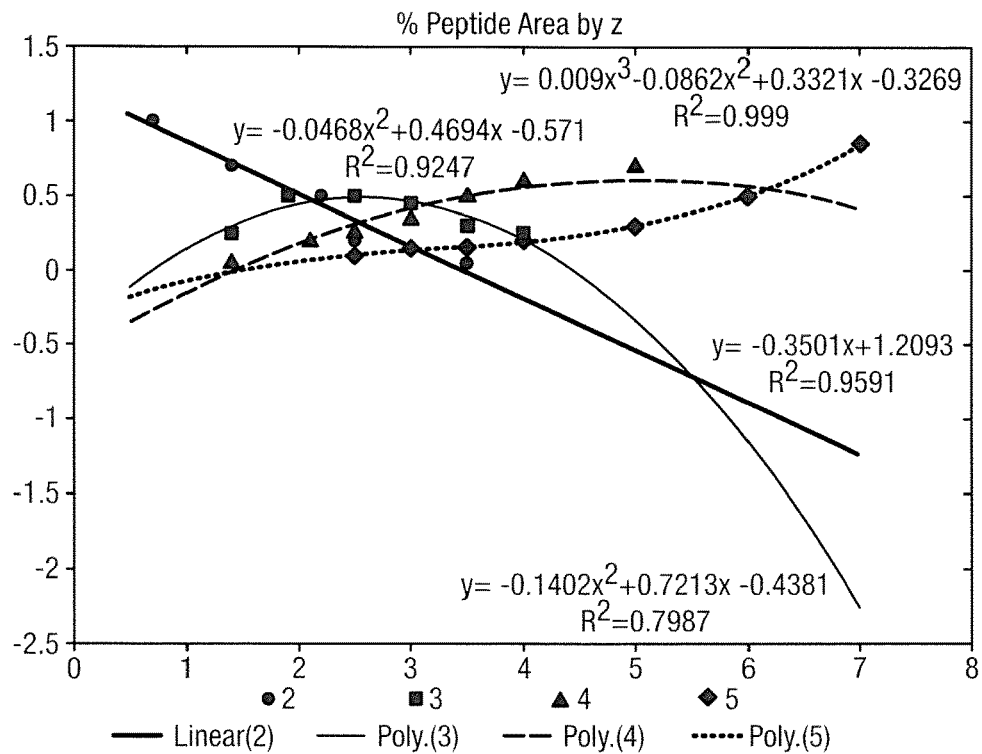

FIG. 4 shows z-distribution and ionisation model updates from matched sequences of mass to charge ratio, chromatographic retention time $t_r$, ion mobility drift time $t_d$ and charge state z.

Figure 5:
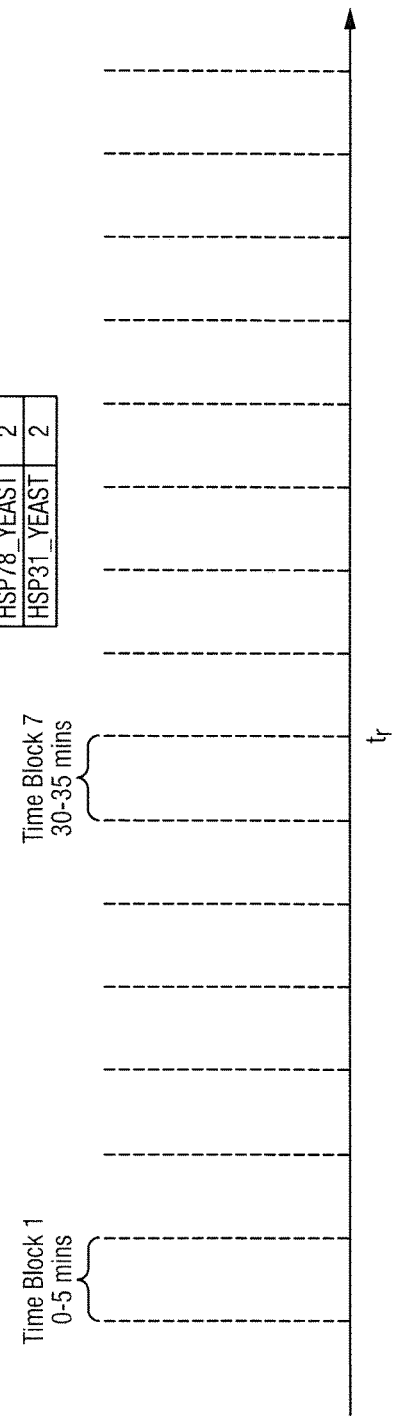
FIG. 5 shows how the elution time may be segmented into user defined or algorithmically derived time blocks.
Figure 5:
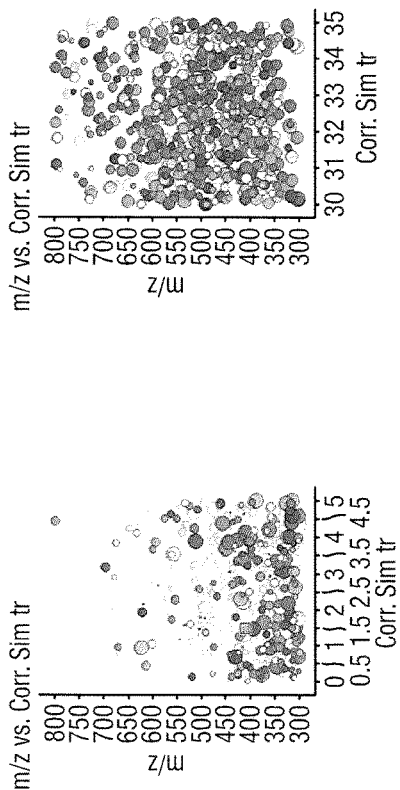

FIG. 5 shows how the elution time may be segmented into user defined or algorithmically derived time blocks. During Time Block 1 (0-5 mins) there are 475 mass to charge values from 353 proteins. Restricting the intact protein molecular weight MW range to 2-25 kDa limits the set to 209 target ions from 162 proteins.

During Time Block 7 (30-35 mins) there are 588 mass to charge values from 463 proteins. Restricting the intact protein molecular weight MW range to 10-100 kDa limits the set to 487 target ions from 348 proteins. At this point 272 proteins and their associated mass to charge ratios are removed since two peptides to each protein have already been validated.

In the 30-35 minute time block 9 Heat Shock proteins were identified and validated and their remaining peptides were removed from the time line.

Figure 6:
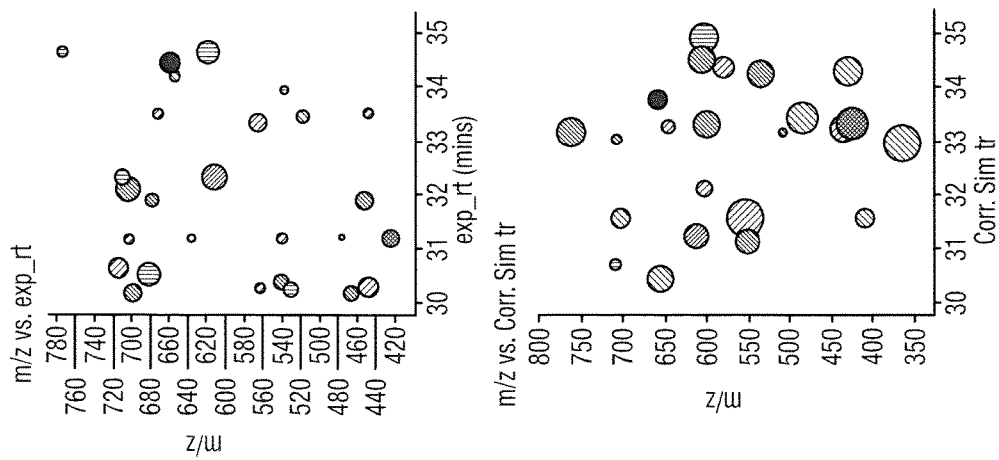
FIG. 6 illustrates the matched data.

FIG. 6 illustrates the matched data and shows how the top three Heat Shock Proteins which were identified match corresponding target proteins.

Although the present invention has been described with reference to various embodiments, it will be understood by those skilled in the art that various changes in form and detail may be made without departing from the scope of the invention as set forth in the accompanying claims.

The invention claimed is:

1. A method of mass spectrometry comprising:
   ionising a sample eluting from a separation device in order to generate a plurality of parent ions;
   generating a target list of ions, wherein said target list comprises a predicted mass to charge ratio and at least one of: a predicted chromatographic retention or elution time; and a predicted ion mobility drift time, cross-sectional area or other data relating to ion mobility, derived from a model;
   performing multiple cycles of operation as said sample elutes from said separation device, wherein each cycle of operation includes mass filtering said parent ions so that selected ions having mass to charge ratios within a first mass to charge ratio range are onwardly transmitted to a fragmentation or reaction device;
   comparing or checking said target list and updating said model; and
   adjusting said first mass to charge ratio range that is used to select ions for onward transmission to said fragmentation or reaction device or adjusting the width of said first mass to charge ratio range that is used to select ions for onward transmission to said fragmentation or reaction device in response to said updated model.

2. A method as claimed in claim 1, further comprising updating said target list so as to no longer select precursor or parent ions which are associated with previously identified parent compounds or updating said target list to select precursor or parent ions which are not associated with previously identified parent compounds.

3. A method as claimed in claim 1, further comprising processing said target list and generating an initial time line.

4. A method as claimed in claim 3, further comprising sorting target ions by chromatographic retention or elution time or the intensity of the A0 molecular ion of each charge group.

5. A method as claimed in claim 3, wherein the step of generating said initial time line further comprises using peptide ionisation rank information.

6. A method as claimed in claim 3, wherein the step of generating said initial time line further comprises prioritizing higher ionizing peptides from lower molecular weight proteins.

7. A method as claimed in claim 1, wherein each cycle of operation includes mass filtering said parent ions based on said target list so that selected ions having mass to charge ratios within a first mass to charge ratio range are onwardly transmitted to a fragmentation or reaction device.

8. A method as claimed in claim 1, wherein each cycle of operation further includes fragmenting or reacting said selected ions in or within said fragmentation or reaction device so as to form fragment or product ions.

9. A method as claimed in claim 1, wherein each cycle of operation further includes obtaining parent ion or fragment or product ion mass spectral data.

10. A method as claimed in claim 1, wherein said step of comparing or checking said target list further includes identifying parent compounds using ion mass spectral data.

11. A method as claimed in claim 1, wherein said target list further comprises a predicted fragmentation pattern derived from a model.

12. A method as claimed in claim 1, wherein said model includes at least one of: a mass to charge ratio model; a chromatographic retention or elution time model; an ion mobility drift time model; and a fragmentation model.

13. A method as claimed in claim 1, wherein each cycle of operation further includes separating or selecting parent ions or fragment or product ions according to their ion mobility.

14. A method as claimed in claim 13, further comprising adjusting a first ion mobility drift time range used to select parent ions or fragment or product ions or adjusting the width of a first ion mobility drift time range used to select parent ions or fragment or product ions in response to said updated model.

15. A method as claimed in claim 1, wherein said model is updated based on at least one of: a derived relationship between (i) modelled chromatographic retention or elution times and (ii) operational or experimental chromatographic retention or elution times; and a derived relationship between (i) modelled ion mobility drift times and (ii) operational or experimental ion mobility drift times.

16. A method as claimed in claim 15, wherein said derived relationship is derived using a line of best fit.

17. A mass spectrometer comprising:

an ion source arranged and adapted to ionise a sample eluting from a separation device in order to generate a plurality of parent ions; and a control system arranged and adapted:

(i) to generate a target list of ions, wherein said target list comprises a predicted mass to charge ratio and at least one of: a predicted chromatographic retention or elution time; and a predicted ion mobility drift time, cross-sectional area or other data relating to ion mobility, derived from a model;

(ii) to perform multiple cycles of operation as said sample elutes from said separation device, wherein each cycle of operation includes mass filtering said parent ions so that selected ions having mass to charge ratios within a first mass to charge ratio range are onwardly transmitted to a fragmentation or reaction device;

(iii) to compare or check said target list and update said model; and (iv) to adjust said first mass to charge ratio range that is used to select ions for onward transmission to said fragmentation or reaction device or to adjust the width of said first mass to charge ratio range that is used to select ions for onward transmission to said fragmentation or reaction device in response to said updated model.

* * * * *